US006653066B1

(12) United States Patent
Krutzik

(10) Patent No.: US 6,653,066 B1
(45) Date of Patent: Nov. 25, 2003

(54) DEVICE AND METHOD FOR DETECTING POLYVALENT SUBSTANCES

(75) Inventor: Siegfried R. Krutzik, Costa Mesa, CA (US)

(73) Assignee: Trinity Biotech, Bray (IE)

( * ) Notice: Subject to any disclaimer, the term of this patent is extended or adjusted under 35 U.S.C. 154(b) by 0 days.

(21) Appl. No.: 08/261,639

(22) Filed: Jun. 17, 1994

(51) Int. Cl.7 .................................................. C12Q 1/70
(52) U.S. Cl. ............................ 435/5; 435/7.1; 435/7.9; 435/7.92; 435/7.94; 435/7.95; 435/971; 435/973; 435/974; 435/967; 436/825; 436/536; 436/541; 436/544; 436/545; 436/546; 436/548; 436/63; 436/811; 436/809; 436/810; 423/55; 423/56; 423/58; 423/60
(58) Field of Search ............................ 435/5, 7.1, 7.9, 435/7.92, 7.94, 7.95, 971, 973, 974, 967; 436/825, 536, 541, 544, 545, 546, 548, 63, 811, 809, 810; 422/55, 56, 57, 58, 60

(56) References Cited

U.S. PATENT DOCUMENTS

| 4,094,647 A | | 6/1978 | Deutsch et al. | |
| 4,235,601 A | | 11/1980 | Deutsch et al. | |
| 4,256,693 A | * | 3/1981 | Kondo et al. | ........ 422/56 |
| 4,313,734 A | | 2/1982 | Leuvering | |
| 4,446,232 A | | 5/1984 | Liotta | |

(List continued on next page.)

FOREIGN PATENT DOCUMENTS

| CA | 1305411 | | 10/1987 | |
| CA | 2057693 | | 12/1991 | |
| CA | 2058019 | | 12/1991 | |
| EP | 0293947 | | 3/1988 | |
| EP | 0262328 | | 4/1988 | |
| EP | 0291194 | | 4/1988 | |
| EP | 0291194 | | 11/1988 | |
| EP | 0299428 | | 1/1989 | |
| EP | 0306772 | | 3/1989 | |
| EP | 313986 | | 5/1989 | |
| EP | 0323605 | | 12/1989 | |
| EP | 0284232 | | 6/1995 | |
| GB | 2204398 | | 11/1988 | |
| GB | 2239313 | * | 6/1991 | ........ G01N/33/543 |
| WO | 9222797 | * | 12/1992 | ........ G01N/30/00 |

OTHER PUBLICATIONS

Gnann et al. 1987 Science 237:1346–1349.*
Berry et al, "A Comparison of Four Enzyme Immunoassays for the Simultaneous Detection of HIV–1– and HIV–2–Specific Antibody", *Journal of Virological Methods*, vol. 34 (1991), pp. 91–100.*
Kramer, et al.; Lymphokine Research, vol. 5, Supplement 1, 1986; "Comparison of TNF–α and TNF–β Cytolytic Biological Activities in a Serum Free Bioassay"; pp. S139–S143.

(List continued on next page.)

*Primary Examiner*—Jeffrey Stucker
(74) *Attorney, Agent, or Firm*—Knobbe Martens Olson & Bear LLP

(57) ABSTRACT

Disclosed is a device and method of use for detecting polyvalent analytes such as antibody to the AIDS virus, utilizing an inverse sandwich method. The test device comprises a first substance having an epitope, bound to a label and capable of moving within the test device. The test device further comprises a second substance immobilized to the test device and spatially separated from the first substance. The second substance has an epitope substantially similar to the epitope of the first substance. Upon application to the test device, the polyvalent analyte binds to the first substance and moves within the test device to the location of the second substance with both polyvalent analyte and first substance are immobilized at location of the second substance. Polyvalent analyte is detected by the presence of the label at the location of the second substance. Also disclosed is a control substance for use with the device that can be used to determine completion of the test and viability of the device.

14 Claims, 4 Drawing Sheets

U.S. PATENT DOCUMENTS

| | | | |
|---|---|---|---|
| 4,447,529 A | | 5/1984 | Greenquist et al. |
| 4,459,358 A | | 7/1984 | Berke |
| 4,486,530 A | | 12/1984 | David et al. |
| 4,670,381 A | | 6/1987 | Frikey et al. |
| 4,703,017 A | | 10/1987 | Campbell et al. |
| 4,740,468 A | * | 4/1988 | Weng et al. .................... 435/7 |
| 4,857,453 A | | 8/1989 | Ullman et al. |
| 4,861,711 A | | 8/1989 | Friesen et al. |
| 4,868,108 A | | 9/1989 | Bahar et al. |
| 4,870,005 A | | 9/1989 | Akiyoshi et al. |
| 4,879,215 A | | 11/1989 | Weng et al. |
| 4,938,927 A | | 7/1990 | Kelton et al. |
| 4,956,302 A | | 9/1990 | Gordon et al. |
| 4,959,305 A | | 9/1990 | Woodrum |
| 4,960,691 A | | 10/1990 | Gordon et al. |
| 4,966,856 A | | 10/1990 | Ito et al. |
| 5,039,604 A | * | 8/1991 | Papsidero .................... 435/5 |
| 5,039,607 A | | 8/1991 | Skold et al. |
| 5,073,340 A | | 12/1991 | Covington et al. |
| 5,073,484 A | | 12/1991 | Swanson et al. |
| 5,089,391 A | | 2/1992 | Buechler et al. |
| 5,120,643 A | | 6/1992 | Ching et al. |
| 5,141,875 A | | 8/1992 | Kelton et al. |
| 5,143,852 A | | 9/1992 | Valkirs et al. |
| 5,164,294 A | | 11/1992 | Skold et al. |
| 5,204,061 A | | 4/1993 | Covington et al. |
| 5,232,835 A | | 8/1993 | Litman et al. |
| 5,232,859 A | | 8/1993 | Kapmeyer et al. |
| 5,248,619 A | | 9/1993 | Skold et al. |

OTHER PUBLICATIONS

Protzman, et al.; Journal of Immunological Methods, 75 (1984), pp. 317–323; "A RadioImmunologic Technique to Screen for Antibodies to α–2 Interferon".

Kramer et al.; Journal of Immunological Methods, 93, (1986) pp. 201–206; "Serum–free in vitro bioassay for the detection of tumor necrosis factor".

Smith, et al.; The Journal of Infectious Diseases; vol. 157, No. 4, Apr. 1988; pp. 812–816; Concise Communications; "Simultaneous Detection of Antibody to the Human Immunodefiency Virus and of the Surface Antigen of Hepatitis B Virus in Human Serum".

Palleroni, et al.; Journal of Interferon Research 6:705–712 (1986); "A Sensitive Radioimmunoassay for Detection of Antibodies to Reombinant Human Interferon–αA"; pp. 705–712.

Chen, et al.; Journal of Radioimmunopreciptation Assay for the Detection of Antibody to Recombinant Human Gamma–Interferon: Comparison to a Bioassay Neutralization Test ; pp. 313–320.

Lamche et al.; Journal of Immunological Methods, 131 (1990) 283–289; pp. 283–289; "Highly Sensitive enzyme immunoassays for antibodies to human tumor necrosis factor (TNF–α) and lymphotoxxin (TNF–β)".

Hennes, et al.; Journal of Biological Standardization (1987) 15, 231–244; "The detection of antibodies to recombinant interferon alfa–2a in human serum".

Pauly, et al.; Behring Inst. Mitt., No. 90, 112–125 (1991); "Highly Specific and Highly Sensitive Enzyme Immynoassay for Antibodies to Human Interleukin 3 (IL–3) and Human Erythrpoietin (EPO) in Serum".

Eiffert, et al., "Use of Peroxidase–labelled Antigen for the Detection of Antibodies to Borrelia burgdorferi in Human and Animal Sera", *Scand J Infect Dis*, 23: 79–81, 1991.

Wide, "Noncompetitive Versus Competitive Binding Assays", *Principles of Competitive Protein–Binding Assays*, Chapter 13, pp. 243–254, 1971.

* cited by examiner

DEVICE AND METHOD FOR DETECTING POLYVALENT SUBSTANCES

FIELD OF THE INVENTION

The present invention relates to devices and methods for the detection or quantification of polyvalent substances such as immunoglobulin, and more particularly to devices and methods for performing inverse sandwich assays for the detection or quantification of polyvalent substances such as immunoglobulin.

BACKGROUND OF THE INVENTION

There are a wide variety of naturally occurring and synthetically produced polyvalent substances of scientific and commercial interest. Prototypical of such substances are immunoglobulin or antibody, which are proteins usually existing as glycoproteins in vivo. The protein moiety of an immunoglobulin comprises a basic unit of two light polypeptide chains and two heavy polypeptide chains, for a total of four polypeptide chains. An immunoglobulin molecule can have more than one of these basic units or can incorporate polypeptide chains in addition to those found as part of a basic unit.

One function of an immunoglobulin molecule is to bind to a substance at a site on the substance called an "epitope". The "epitope binding site" on an immunoglobulin molecule is comprised of a segment of one light polypeptide chain and a segment of one heavy polypeptide chain such that the basic unit of four polypeptide chains defines two epitope binding sites.

Naturally occurring immunoglobulins are divided into classes and subclasses on the basis of amino acid sequence differences in the heavy polypeptide chain. In humans, there are five classes, IgD, IgE, IgG each having two epitope binding sites, IgA having two or four epitope binding sites, and IgM having ten epitope binding sites.

Antibodies are of particular scientific and commercial interest among the types of polyvalent substances because of their role in the mammalian immune response. They are markers of current and past infection, and important in host reactions against foreign substances such as viruses, bacteria, tissue grafts, toxins and drugs. Further, the inappropriate production of antibodies against host tissues contributes to many diseases including myasthenia gravis, hemolytic anemia, scleroderma, Graves' disease and rheumatoid arthritis.

Because of their importance, a variety of methods have been developed for the detection or quantification of antibody, including an antiviral neutralization bioassay and a radioimmunoassay. In most antibody detection or quantification methods, sample containing analyte antibody is applied to the surface of a device having an suitable immobilized antigen on the surface. The analyte antibody is allowed to bind to the immobilized antigen creating immobilized antigen/analyte antibody complexes. A ligand is then applied to the immobilized antigen/analyte antibody complex-coated surface and binds to the analyte antibody of the immobilized antigen/analyte antibody complex at a site other than one of the analyte antibody molecules' epitope binding sites. The ligand contains a chromogen, enzyme or radioactive label. Detection of the chromogen, enzyme or radioactive label remaining on the surface is a measure of the presence or quantity of the analyte antibody.

More recently, there has been described a sandwich-type of enzyme immunoassay for the detection or quantification of antibody, dubbed an "inverse sandwich" immunoassay. This assay utilizes the presence of the two epitope binding sites on an immunoglobulin molecule which allows each immunoglobulin molecule to simultaneously bind to two separate antigen moieties having a substantially-identical epitope.

In the inverse sandwich immunoassays heretofore described, an antigen is immobilized to the surface of plastic beads or a microtitre plate. Disadvantageously, the known techniques for utilizing an inverse sandwich immunoassay for the detection or quantification of immunoglobulin requires specialized equipment not readily available to a consumer or present in a physician's office. A further disadvantage of these prior techniques of performing an inverse sandwich immunoassay using beads or microtitre plates is that tight control is required over several of the parameters involved in performing the assay. Also disadvantageously, using beads or microtitre plates to perform an inverse sandwich immunoassay necessitates one or two washing steps.

SUMMARY OF THE INVENTION

According to one aspect of the present invention, there is provided a device for detecting the presence or amount of analyte antibody in a sample. The device includes a first zone that includes a first matrix and a first substance that includes an epitope that is capable of binding to the analyte antibody. The first substance has a label. The device further includes a second zone spatially separate from the first zone and in fluid communication with the first zone. The second zone includes a second matrix and a second substance that includes an epitope substantially identical to the epitope on the first substance. The second substance is immobilized on the second matrix and the first substance is capable of moving from the first zone to the second zone after application of the sample to the first zone.

According to another aspect of the present invention, the device can be used to detect antibody to Human Immunodeficiency Virus (HIV). In one preferred embodiment, the device can detect the presence or amount of antibody to HIV-1 glycoprotein 41. In another preferred embodiment, the device can detect the presence or amount of antibody to HIV-2 glycoprotein 36.

According to another aspect of the present invention, there is provided a method for detecting the presence or amount of analyte antibody to Human Immunodeficiency Virus in a sample. First, a device according to one of the foregoing aspects of the present invention is provided. Next, sample is applied to the first zone, the antibody in the sample comprising first and second epitope binding sites. After binding the first epitope binding site on the analyte antibody to the first epitope on the first substance, thereby forming an analyte antibody/first substance complex, the complex is allowed to migrate from the first zone to the second zone. Next, the second epitope binding site on the analyte antibody of the first substance/analyte antibody is allowed to bind to the second epitope on the immobilized second substance in the second zone, thereby forming immobilized first substance/analyte antibody/second substance. Finally, the label upon the first substance of the immobilized first substance/analyte antibody/second substance is detected. In a preferred embodiment, the label includes a chromogen and the detecting step includes visually identifying a color change on the second zone.

In another aspect of the invention, there is provided a device for detecting the presence or amount of analyte antibody to each of two antigens, antigen-1 and antigen-2, in a sample. In a preferred embodiment, antigen-1 is Human Immunodeficiency Virus 1 and antigen-2 is Human Immunodeficiency Virus 2. The device includes a first zone that includes a first matrix, an antigen-1 first substance and an antigen-2 first substance. The antigen-1 first substance includes an epitope from antigen-1, and the antigen-2 first substance includes an epitope from antigen-2. Each of the first substances has a label. The device further includes a second zone spatially separate from the first zone and in fluid communication with the first zone. The second zone includes a second matrix, an antigen-1 second substance and an antigen-2 second substance. The antigen-1 second substance includes an epitope from antigen-1 that is substantially identical to the epitope from antigen-1 on the antigen-1 first substance. The antigen-2 second substance includes an epitope from antigen-2 that is substantially identical to the epitope from antigen-2 on the antigen-2 first substance an epitope. Each of the second substances is immobilized on the second matrix. Each of the first substances is capable of moving from the first zone to the second zone after application of the sample to the first zone. In one particularly preferred embodiment, the first substance and each second substance include at least one substance selected from the group consisting of HIV-1 glycoprotein 41, HIV-2 glycoprotein 36, and a fragment, derivative or combination of any of the foregoing.

In yet another aspect of the invention, there is provided a device for detecting the presence or amount of a polyvalent analyte in a sample. The device includes a first zone that includes a first matrix and a first substance. The first substance has a label. The device further includes a second zone that includes a second matrix and a second substance. The second substance is immobilized to the second matrix. The second zone is spatially separate from the first zone and in fluid communication with the first zone. The first substance is in relation to the first matrix such that the first substance is capable of moving from the first zone to the second zone after application of the sample to the first zone. A first epitope binding site and a second epitope binding site on the analyte antibody are capable, respectively, of sequentially binding to a first epitope on the first substance and a second epitope on the second substance, such that, after the completion of both bindings, both epitope binding sites are simultaneously occupied. Further, the first epitope on the first substance and the second epitope on the second substance are substantially identical.

The devices provided according to the several aspects of the present invention may additionally include a control substance.

DETAILED DESCRIPTION OF THE PREFERRED EMBODIMENTS

Figure 1:
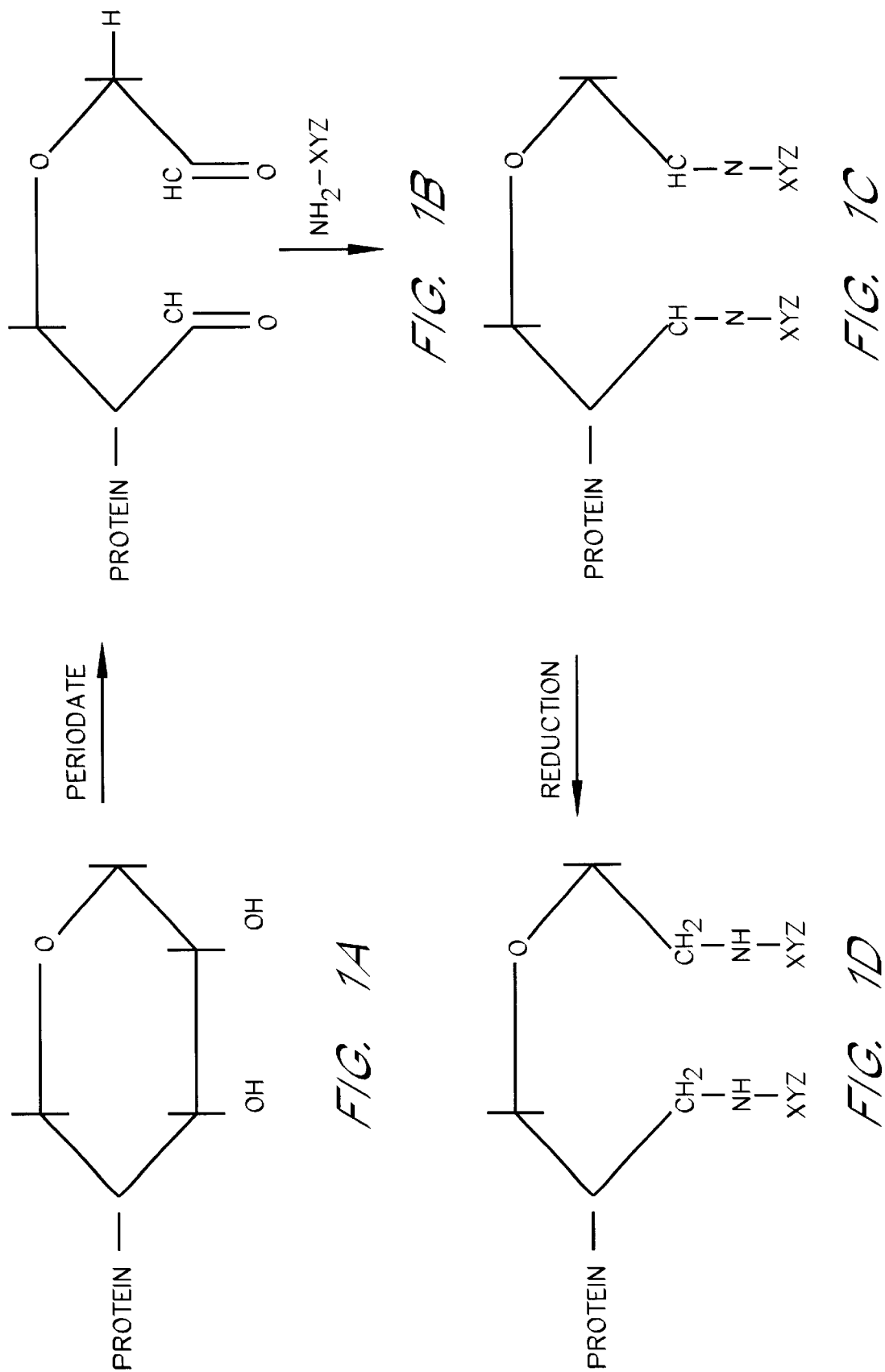
FIG. 1 is a schematic representation of a chemical reaction used in manufacturing an embodiment of the present invention.

The inverse sandwich enzyme immunoassay method has several advantages over other available antibody detection or quantification methods. First, it detects or quantifies antibody independent of the species-origin of the antibody because equivalent binding sites on an antibody molecule from any species will simultaneously bind two antigen moieties having substantially-identical, appropriate epitopes. This species-independence characteristic of the inverse-sandwich immunoassay is a great advantage in industries such as the pharmaceutical industry where it is necessary to study the immune reaction of multiple species.

Another advantage of the inverse sandwich immunoassay technique is that human antibody is not required to standardize the assay because the technique is species-independent. This is useful because a suitable preparation of human antibody is often unavailable.

Still another advantage of the inverse sandwich immunoassay is that it requires analyte antibody molecules to specifically bind to two substantially-identical epitopes in order for the analyte antibody to be detected. Thus, non-specific binding of analyte antibody to the solid support will not result in a detectible signal, which results in reduced background noise.

In one form of inverse sandwich assay, a first antigen is immobilized to the surface of plastic beads or a microtitre plate. The immobilized first antigen has an epitope capable of being bound by either of the at least two epitope binding sites on an analyte antibody molecule. Sample potentially containing the analyte antibody is applied to the surface coated with immobilized first antigen and the analyte antibody is allowed to bind to the immobilized first antigen through either of each analyte antibody molecules' at least two epitope binding sites. This creates immobilized first antigen/analyte antibody complexes.

Next, non-analyte sample components and unbound analyte are washed from the surface. A reagent is applied to the surface having the immobilized first antigen/analyte antibody complexes. The reagent contains a second antigen comprising a substantially-identical epitope as the immobilized first antigen and an enzyme label bound to the second antigen. The second antigen-label binds to at least some of the at least two available epitope binding sites on the analyte antibody molecules not bound to the immobilized first antigen, thus creating immobilized first antigen/antibody/second antigen-label complexes. Unbound reagent is washed off and substrate for the enzyme label on the second antigen is applied to the bound immobilized first antigen/antibody/second antigen-label complexes. Tight control is required over the amount of the second antigen-label complex added to the solid support, and over the time at which the reagent containing the second antigen-label is added after applying the sample. Detection or quantification of the antibody is made by detecting a signal produced by the label and substrate.

As discussed above, prior art inverse sandwich assays making use of microtiter plates or solid beads suffer from a number of disadvantages. It is one goal of the present invention to provide a device and method for the detection or quantification of a polyvalent analyte, such as an antibody, which is sensitive, rapid, simple and versatile. In one embodiment, the present invention discloses a device and method which utilize the inverse sandwich principle but avoids some of the disadvantages inherent in using beads or microtitre plates as the solid support through improvements described herein. In one preferred embodiment, the device and method are used to detect the presence of antibody to human immunodeficiency virus. One important improvement made to the inverse sandwich immunoassay by the present invention relates to the spatial separation of the location of the two binding steps.

One aspect of the present invention provides a rapid method for performing an inverse sandwich assay that overcomes the disadvantages of prior art such assays. One inventive device which allows this method to be implemented provides for the detection or quantification of a polyvalent analyte. This device includes a first matrix having a mobile first substance thereupon and a second matrix having an immobilized second substance thereupon. The first and second matrix are in fluid communication with each other. Sample containing analyte antibody is applied to the first matrix and binds to the first substance. The analyte antibody bound to the first substance moves to the second matrix where it additionally binds to the immobilized second substance. Detection of the presence of the analyte antibody at the location of the second substance is made by a label on the first substance.

As used herein, "polyvalent substance" and "polyvalent analyte" interchangeably refer to a chemical substance having two or more "epitope binding sites", each epitope binding site capable of binding to an "antigenic determinant" or "epitope", wherein at least two of the epitope binding sites on a polyvalent substance are capable of binding to substantially-identical epitopes either sequentially or simultaneously so long as after the binding is completed, both epitope binding sites are simultaneously occupied. As used herein, "simultaneously bind" or a similar phrase refers to the end relationship of the polyvalent substance and epitope, rather than the order in which the binding occurs.

The substantially-identical epitopes can be on either two separate substantially-identical moieties or on two separate substantially non-identical moieties. Thus, a polyvalent substance is capable of at least one of two types of binding. In one type of binding, the polyvalent substance can simultaneously bind an epitope on a first moiety at a first epitope binding site, while binding a substantially-identical epitope on a substantially-identical second moiety at a second epitope binding site. In a second type of binding, a polyvalent substance can simultaneously bind an epitope on a first moiety at a first epitope binding site, while binding a substantially-identical epitope on a substantially non-identical second moiety at a second epitope binding site.

A polyvalent substance can include epitope binding sites in addition to the two epitope binding sites for substantially identical first and second epitopes of a first and second moiety. These additional epitope binding sites can also bind epitopes that are substantially identical to the first and second epitopes, or in the alternate, can bind epitopes that are substantially non-identical to the first and second epitopes. Non-limiting examples of polyvalent substances include antibodies and receptors.

As used herein, "immunoglobulin" and "antibody" are interchangeably intended to refer to a substance or substances having the four amino acid chain basic unit described above, including IgA, IgE, IgG, IgM, which are normally produced by a host organism in response to an antigen, and which have at least two epitope binding sites, each capable of specific binding with an antigen at a binding site on the antigen referred to interchangeably as an "antigenic determinant" or "epitope". "Immunoglobulin" and "antibody" also interchangeably refer to cell surface markers and receptors which comprise the four polypeptide chain unit described above, such as IgD, and to structurally substantially similar naturally occurring and synthetically produced compounds, regardless of their function. As used herein "synthetic" and "synthetically" encompass both biosynthetic, non-natural production and nonbiosynthetic, non-natural production.

"Immunoglobulin" and "antibody" further interchangeably refer to a fragment or fragments of a substance which, in the non-fragment form has the four amino acid chain unit, and which in the fragment form has the ability to simultaneously bind an epitope on a first antigen at a first epitope binding site on the fragment, while binding a substantially-identical epitope on a second antigen, substantially-identical with the first antigen, at a second epitope binding site on the fragment; or wherein the fragment has the ability to simultaneously bind an epitope on a first antigen at a first epitope binding site on the fragment, while binding a substantially-identical epitope on a second antigen, substantially non-identical with the first antigen, at a second epitope binding site on the fragment.

As used herein, "epitope binding site" refers to a chemical sequence, chemical group or chemical structure capable of specific binding with an epitope or antigenic determinant through non-covalent bonds, regardless of whether the strength of the bond is lesser, equal to or greater than a covalent bond. On an antibody molecule, the epitope binding site refers to one of the at least two chemical structures formed by a segment of one light polypeptide chain and a segment of one heavy polypeptide chain which are capable of specific binding to an epitope on an antigen. The epitope binding site of a non-immunoglobulin polyvalent substance can be composed of a chemical structure similar to that of an immunoglobulin molecule or can be of any other chemical structure capable of an equivalent function.

As used herein, "epitope" and "antigenic determinant" are interchangeably intended to refer to a chemical sequence, chemical group or chemical structure that is capable of being bound to an epitope binding site on an immunoglobulin molecule or other polyvalent substance.

As used herein, "antigen" refers to any substance to which a host immune system mounts an immune response, or more generally, to any substance having an epitope such that a polyvalent analyte is capable of binding the epitope at either of the at least two epitope binding sites present on the polyvalent analyte. Non-limiting examples of antigens comprise one or more of the following, or a fragment or derivative of one or more of the following, whether naturally existing or synthetically produced: proteins, glycoproteins, fatty acids, lipids, polynucleotides, ribonucleic acids, deoxyribonucleic acids, hormones, enzymes, viruses, bacteria, prokaryotic cells and eukaryotic cells.

As used herein, "fragment" refers to any part or parts of a substance, less than the whole substance.

As used herein, human immunodeficiency virus (HIV) refers to any of the class of retroviruses capable of causing acquired immunodeficiency syndrome in a human or the equivalent disease in an animal, or any fragment, derivative or attenuated form of the virus, such as in an immunization preparation, whether naturally occurring or synthetically or recombinantly produced, or any combination of the foregoing.

In one aspect, the present invention includes a device for the detection or quantification of a polyvalent analyte. The device includes at least two zones, a first zone and a second zone. The first zone comprises a first matrix and the second zone comprises a second matrix. The first zone is spatially separated from the second zone and in fluid communication with the second zone.

The first zone additionally comprises a first substance. The second zone additionally comprises a second substance. The first substance has a first epitope capable of being bound by either of a first epitope binding site or a second epitope binding site of the at least two epitope binding sites on the polyvalent analyte. The second substance has a second epitope capable of being bound by either of a first epitope binding site or a second epitope binding site of the at least two epitope binding sites on the polyvalent analyte.

The polyvalent analyte can bind the first epitope on the first substance at the first epitope binding site and the second epitope on the second substance at the second epitope binding site simultaneously. The polyvalent analyte can also bind the first epitope on the first substance at the second epitope binding site and the second epitope on the second substance at the first epitope binding site simultaneously.

The first substance can be substantially identical or substantially non-identical with the second substance. However, the first epitope and the second epitope are substantially identical.

The first substance is in relation to the first matrix such that the first substance is capable of moving from the first zone to the second zone. The second substance is immobilized to the second zone.

The first substance additionally comprises a label. Detection or quantification of the label serves as a means for detecting or quantifying the polyvalent analyte. The label comprises any of a variety of substances known to those with skill in the art, including but not limited at least one substance selected from the group consisting of an enzyme, a radioactive substance, a florescent compound, a chromogen, colored latex, gold particles such as colloidal gold, a peroxidase, a textile dye, alkaline phosphatase, $\alpha$-glucosidase, $\beta$-galactosidase, glucose oxidase, urease, a fragment thereof and a combination thereof. The label can be bound to the first substance by covalent or non-covalent forces, such as by hydrophobic bonding.

One method of use of the device for detecting or quantifying polyvalent analyte according to the present invention is in the following manner. Sample potentially containing polyvalent analyte is applied to the first zone comprising the first matrix and first substance having a label. If polyvalent analyte is present in the sample, at least some polyvalent analyte moieties will bind to the first substance at the first epitope by at least one of the epitope binding sites on the polyvalent analyte, thereby, forming polyvalent analyte/first substance-label complexes.

The first matrix is porous and of such construction that at least some of the polyvalent analyte/first substance-label complexes will flow through the first zone to the second zone. Flow can be unidirectional, only towards the second zone, or multidirectional. Flow in the direction of the first zone to the second zone is considered positive flow. Multidirectional flow, that is positive flow and non-positive flow, can be both towards the second zone and away from the second zone, or towards the second zone and in a direction neither towards nor away from the second zone, or a combination thereof. Flow can be accomplished by capillary action, suction, the addition of non-sample fluid or by other means as well be understood by those with skill in the art.

Flow rate is dependent on temperature. Generally, the higher the temperature, the faster the flow. Therefore, according to one aspect of the present invention, detection or quantification of polyvalent analyte can be accomplished more quickly by raising the temperature surrounding the device.

The second matrix can be the same material and construction as the first matrix, that is, the first and second matrix can form a unitary matrix. In the alternate, the first and second matrix can be of different material or different construction. Either matrix can comprise multiple materials of differing constructions. In addition, glazing can be added to the surface of at least one of the matrices and first substance, second substance or an additional substance applied to the surface of the glazing rather than to the unglazed matrix, in order to diminish substance-matrix interactions.

Glazing can be used, for example, to maintain the mobility of the first substance on the first zone prior to application of the sample. Appropriate glazing for this use can comprise aqueous lactose or sucrose or cellulose solution, applied and then dried, upon which the first substance-label would be then be applied.

Upon entering the second zone, at least some of the polyvalent analyte/first substance-label complexes will encounter the immobilized second substance having a second epitope. At least some of the polyvalent analyte moieties on the polyvalent analyte/first substance-label complexes will bind the second epitopes on the immobilized second substances on at one of the at least two epitope binding sites on the polyvalent analyte moieties that is not binding the first epitope on the first substance. The result is the creation of second substance/polyvalent analyte/first substance-label complexes immobilized to the second matrix through the second substance moieties.

Polyvalent analyte/first substance-label complexes not binding to the second substance, unbound sample components, unbound first substance-label complexes and any additional non-second substance components not part of the second substance/polyvalent analyte/first substance-label complexes will continue to flow away from the immobilized second substance on the second zone.

The label on the immobilized second substance/polyvalent analyte/first substance-label complexes is detected or quantified by any of a variety of means appropriate for the label as are readily understood by those with skill in the art. For example, colored labels or "direct labels" can be visually detected without special equipment and can be quantified by visual comparison against a reference color chart. Fluorescent labels or radioactive labels can be detected or quantified using appropriate instruments. Enzyme labels can require the addition of an appropriate enzyme substrate. The enzyme substrate can further comprise an additional label allowing detection in the presence of the enzyme.

In one preferred embodiment, the label comprises gold particles. The use of peptides alone as first substance disadvantageously promotes aggregation of the gold particles. Therefore, certain modifications of peptides to produce first substances as described below advantageously decreases aggregation of gold particles while retaining activity to be bound by the analyte polyvalent substance.

Conjugation of a peptide-based or other first substance to gold particles to produce first substance-label can be accomplished through adsorption alone or through covalent binding. Adsorption depends upon several effects, including electrostatic interaction between the negatively charged surface of the gold particles and positively charged groups of the peptide-based or other substance, hydrophobic attraction between the surface of the gold particles and peptide-based or other substance, and dative binding between the gold conducting electrons and sulphur atoms of the peptide-based or other substance.

The type of conjugation of the peptide-based or other first substance to the gold particles affects the reactivity of the first substance with analyte polyvalent substance. In the case of analyte antibody, the sterical accessibility or molecular orientation of the epitope in the first substance determines, at least in part, both the sensitivity of the test and the binding rate of the analyte antibody to the first substance. The binding rate determines, at least in part, the time required to complete the test.

Peptides containing between about 15 and 30 amino acids vary in their ability to bind to gold particles, depending on the peptides' exact amino acid composition and isoelectric point. Therefore, various modifications can be made to peptide-based or other first substances to improve the yield of stable, usable first substance.

Referring now to FIG. 1, there is illustrated one method of producing the first substance by modifying glycoprotein, whether derived from natural sources or synthetic sources, and linking the modified glycoprotein with the gold particles. Initially, the carbohydrate moiety of the glycoprotein (a) is oxidized using sodium periodate to produce the aldehyde (b) as shown. Next, a substance containing at least one amino group is linked to the aldehyde forming entity (c). Finally, compound (c) is reduced using sodium cyanborohydride to form stable covalent bonds as indicated in (d).

Alternately, another method of producing the first substance involves a heterobifunctional method employing a reaction between maleimide and sufhydryl groups as is understood by those with skill in the art. An example of this method is described in publications by Duncan, R. J. S. et al., Analytical Biochemistry. 132, 68, 1983, Fujiwara, K. et al., *Journal of Immunological Method,* 45, 195, 1981, and Kitagawa, T., et al., *Journal Biochemistry,* 94, 1160, 1983, the disclosures of which are hereby incorporated in their entirety. In summary, a malemide group is joined to the peptide-based or other substance containing the epitope using N-γ-maleidobutyryloxy-succinimide (GMBS). A sulfhydryl group is joined to a carrier substance using N-succinimidyl-S-acetyl-thioacetate (SATA) and hydroxylamine. The two activated molecules are linked together under physiological conditions at room temperature for between about 2 and 10 hours. After preparation of the first substance, it is combined with gold particles by the method described in detail below.

Detection of the label on the immobilized second substance/polyvalent analyte/first substance-label complexes is an indirect indication of the presence of the polyvalent substance bound in the second zone and, hence, present in the sample. Quantification of the label on the immobilized second substance/polyvalent analyte/first substance-label complexes is an indirect indication of the quantity of the polyvalent substance bound in the second zone and, hence, present in the sample or applied to the device. As used herein, "amount" can be taken to mean concentration, activity, quantity, titre and a related measure or a combination thereof.

The first zone of the device for the detection or quantification of polyvalent analyte can comprise at least two zones, a sample application region and a separation zone, with or without additional zones. The sample application zone serves as a site for application of the sample. The separation zone serves to separate the sample application zone from the second zone. The first substance can be located in the sample application zone, in the separation zone, in other zones at least partly comprising the first zone or in a combination of zones at least partly comprising the first zone. If the first zone comprises at least two zones, the first matrix can also comprise at least two matrices, each matrix having a unique composition or pore size.

The second zone of the device for the detection or quantification of polyvalent analyte can comprise at least two zones, a detection zone and a collection zone, with or without additional zones. The detection zone serves to contain the immobilized second substance. The collection zone serves to draw away from the detection zone polyvalent analyte/first substance-label complexes not binding to the second substance, unbound sample components, unbound first substance-label complexes and any additional non-second substance components not part of the second substance/polyvalent analyte/first substance-label complexes. If the second zone comprises at least two zones, the second matrix can also comprise at least two matrices, each matrix having a unique composition or pore size.

The device for the detection or quantification of polyvalent analyte can be constructed to allow the detection or quantification of multiple polyvalent analytes in a sample or samples. Detection and quantification of multiple polyvalent analytes means that the device can be used to distinguish the individual presence or quantity of each of two or more polyvalent analytes in a sample or samples, or means that the device can be used only to determine if at least one of the polyvalent analytes of two or more polyvalent analytes is present or the amount of a combination of at least two polyvalent analytes.

One way for the device to be used to distinguish the individual presence or quantity of multiple polyvalent analytes in a sample or samples containing at least two polyvalent analytes, is to provide at least one second substance immobilized in the second zone for each polyvalent analyte to be individually detected or quantified. The second substances can occupy the same portion of the second zone or different portions of the second zone. If they occupy different portions of the second zone, they can be linearly arrayed, horizontally arrayed, vertically arrayed or a combination or variation thereof. If they occupy the same portion of the second zone then the labels on the corresponding first substances must be distinguishable from one another when the labels occupy the same space.

For example, in order to determine the presence or quantity of polyvalent analyte #1 and polyvalent analyte #2 from a single or multiple samples, the device can be constructed with two first substances, first substance #1 and first substance #2, each having a label, label #1 and label #2, respectively, in the first zone. First substance #1 and first substance #2 can occupy the same space in the first zone, different spaces in the first zone or overlapping spaces in the first zone. Application of the sample or samples containing polyvalent analyte #1 and polyvalent analyte #2 to the first zone produces polyvalent analyte #1/first substance #1-label #1 complexes and polyvalent analyte #2/first substance #2-label #2 complexes. At least some of these two complexes will flow from the first zone to the second zone where they will encounter second substance #1 and second substance #2 immobilized in the matrix of the second zone. At least some of polyvalent analyte #1 and polyvalent analyte #2 will bind to immobilized second substance #1 and immobilized second substance #2 respectively through one of their at least two epitope binding sites to produce immobilized second substance #1/polyvalent analyte #1/first substance #1-label #1 complexes and immobilized second substance #2/polyvalent analyte #2/first substance #2-label #2 complexes. Polyvalent analyte/first substance-label complexes not binding to the second substance, unbound sample components, unbound first substance-label complexes and any additional non-second substance components not part of the second substance/polyvalent analyte/first substance-label complexes will continue to flow away from the immobilized second substances.

Polyvalent analyte #1 and polyvalent analyte #2 are detected or quantified indirectly by detecting or quantifying label #1 and label #2 of the immobilized second substance #1/polyvalent analyte #1/first substance #1-label #1 complexes and immobilized second substance #2/polyvalent analyte #2/first substance #2-label #2 complexes, by analogous methods described above for detecting or quantifying a single polyvalent analyte, as will be understood by those with skill in the art.

A second way for the device to be used to distinguish the individual presence or quantity of multiple polyvalent analytes in a sample or samples containing at least two polyvalent analytes, is to provide at least one label for each polyvalent analyte to be individually detected or quantified, even though there is only a single second substance immobilized in the second zone. In this aspect of the present invention, detection or quantification of the label corresponding to each polyvalent analyte among the immobilized second substance/polyvalent analyte/first substance-label complexes will indirectly detect or quantify the amount of each polyvalent analyte present in the sample or samples. As will be readily appreciated by those with skill in the art, the labels can be of differing types, such as a fluorescent label and a chromogen, or can be of the same type, such as two chromogens, which produce additive effects that are distinguishable for the effect for either label individually.

Three or more polyvalent analytes in a sample or samples can similarly be detected using a device having three or more second substances, three or more labels or a combination thereof, in analogous methods to that used to detect two polyvalent analyte substances. Further, the modifications of the device and method of using the device described above and below for detecting or quantifying a single polyvalent analyte can be adapted for use in detecting or quantifying multiple polyvalent analytes.

Nonlimiting examples of multiple polyvalent analytes suitable for detection or quantification by the device and method according to a preferred embodiment of the present invention include antibodies of significance in pregnancy such as antibodies to toxoplasma, rubella, cytomegalovirus and herpes, antibodies to various common allergens such as antibodies to various pollens, animals, food or components of cosmetics, antibodies to common sexually transmitted diseases such as herpes, AIDS, syphilis, gonorrhea and chlamydia, antibodies involved in autoimmune diseases, and polyvalent analytes produced by damaged cardiac or neurologic tissues.

In a particularly preferred embodiment, the device and method of the present invention is used to detect multiple types of antibodies having specificities for various gene products or modified gene products of HIV-1, HIV-2 or a combination, thereof. Nonlimiting examples of suitable polyvalent analytes include antibodies to HIV-1 core protein 24, transmembrane glycoprotein 41, reverse transcriptase 51 and envelope glycoprotein 120. Using a device according to one aspect of the present invention to detect or quantify these antibodies simultaneously allows an antibody profile to HIV-1 to be determined, similar to a Western blot, as is understood by those with skill in the art. An equivalent antibody profile can be determined for HIV-2 as is understood by those with skill in the art.

A sample can originate from multiple sources, can be taken from the same source at different times, and can be applied together, separately or intermittently. Samples can be derived from any of a variety of fluids, or can be derived from non-fluids and constituted or reconstituted into fluids before application to the device. Non-limiting examples of samples include blood, serum, plasma, urine, sputum, cell culture supernatant, cell culture suspension, tissue culture supernatant, tissue culture suspension, cerebrospinal fluid, bone marrow, aqueous fluid, lacrimal fluid, saliva, pus, seminal fluid, amniotic fluid, sweat, mammary gland secretion, lymph, intraarticular fluid, pericardial fluid, peritoneal fluid and combinations thereof.

The appropriate pore size or range of sizes present in the first and second matrices, or additional matrices, is determined by a number of factors. In addition to varying pore size, pore configuration can also be varied to promote unidirectional flow, bidirectional flow, or to limit flow in another manner.

Generally, the larger the pore size of the first matrix, the more rapidly the polyvalent analyte/first substance-label complexes flow towards the second zone, which is generally advantageous. However, the larger the pore size, the less surface area in the second matrix is available to immobilize the second substance and contain the first substance, which is generally disadvantageous.

Also a factor in determining an appropriate pore size is the viscosity and particle size present in the sample fluid. If the sample contains particles significantly larger than the polyvalent analyte/first substance-label complexes, it can be advantageous to have a first matrix pore size large enough to pass the polyvalent analyte/first substance-label complexes but small enough to filter out unwanted particles present in the sample such that they do not reach the second zone.

For example, in a sample of blood where the analyte is immunoglobulin and the first substance a suitable protein, first matrix pore size can be less than about $5\mu$ in order to retain red cells and white cells in the first zone. Non-limiting examples of sample fluids that can use the matrix pore size to filter out unwanted particles include sputum, bone marrow, pus, seminal fluid, mammary gland secretion, lymph and combinations thereof.

As an alternate to adapting the pore size to act as a filter, the sample can be filtered prior to application to the device or can pass through an adjunct filter covering the sample application site on the first zone. The filter can be made of the same or different material as a matrix, only having a pore size appropriate for the filtering function. The first matrix, second matrix, any additional matrix and the filter, if one is present, can comprise at least one of the following, nitrocellulose, polystyrene, polyvinyl, polycarbonate, nylon, cellulose acetate, glass fiber, filter paper or a combination thereof, as would be appreciated by those with skill in the art. In a preferred embodiment, the matrices are comprised of nitrocellulose, as nitrocellulose is available commercially in a range of pore sizes.

The overall configuration of the device can be any of a number of forms including substantially rectangular, square, oval, round, trapezoidal or any other shape suitable for purposes as would be understood by those in the art. For example, the first and second zone can be in horizontal fluid communication with the first zone occupying one end of a rectangular overall configuration and the second zone occupying the other end of a rectangular overall configuration. Alternately, the first and second zone can be in horizontal fluid communication with the first zone occupying the center of a disc-like overall configuration and the second zone occupying a circumferentially area around the first zone.

In another aspect of the present invention, the device can have first and second zones in vertical fluid communication with each other or in a combination of horizontal and vertical communication with each other.

In another aspect of the present invention, the device for detecting or quantifying the amount of a polyvalent analyte has Y-shaped or other multi-pronged shaped configuration. In this aspect of the present invention, the first zone occupies the lower part of the Y, or central portion of the multi-pronged shape, and the second zone occupying the two upper parts of the Y or multiple prongs of the multi-pronged shape. These configurations can be especially suitable for the simultaneous detection of at least two polyvalent analytes, where each of the corresponding at least two second substances are immobilized in the matrix on one of the prongs. In this form, the label on the multiple first substances can be identical and individual detection or quantification of the multiple polyvalent analytes accomplished by presence or quantity of the label corresponding to each polyvalent analyte in a specific portion of the various prongs. Other variations for the position of the second substances, and hence immobilization site for the label, are described above.

In another aspect of the present invention, the device for detecting or quantifying the amount of a polyvalent analyte also has Y-shaped or other multi-pronged shaped configuration. In this aspect of the present invention, the second zone occupies the lower part of the Y, or central portion of the multi-pronged shape, and multiple first zones occupy the two upper parts of the Y or multiple prongs of the multi-pronged shape. These configurations can be especially suitable for the simultaneous detection of at least two polyvalent analytes, where each of the corresponding at least two first substances and labels are immobilized in the matrix on one of the prongs. In this form, the second substances corresponding to each polyvalent analyte can be identical and individual detection or quantification of the multiple polyvalent analytes accomplished by presence or quantity of the differing label corresponding to each polyvalent analyte in the second zone. Other variations for the position of the second substances, and hence immobilization site for the label, are described above.

Application of the sample to the device can be applied by any of a number of methods as are understood by those with skill in the art. Non-limiting examples include at least one of dipping the device in the sample, dropping the sample on the device, such as for example by a pipette, and inserting the device into a tube containing sample. Further, one end of the device can contain a wick. Dipping the wick in the sample would allow an amount of sample, determined by the properties of the wick, to flow into the first matrix.

Alternately, a non-fluid sample or sample containing insufficient fluid to cause the polyvalent analyte/first substance-label complexes to flow can be applied to the first zone and non-sample fluid applied to the device in at least one manner as would fluid sample be applied, in order to cause the polyvalent analyte/first substance-label complexes to flow to the second zone.

In another aspect of the present invention, the device can contain one or more control zones. Each control zone comprises a control matrix having a control substance immobilized thereupon. The control zone can be part of second zone. In one particularly preferred embodiment, the collection zone comprises the control zone.

In one preferred embodiment, the control substance has the property of binding a corresponding first substance-label, at either the epitope binding site or another site on the first substance or label, and hence immobilizing the first substance-label to the control matrix. The control substance can comprise at least one of a monoclonal antibody, a polyclonal antibody, the polyvalent analyte and a fragment thereof.

The control substance can be the same as the polyvalent analyte, but does not need to be the same. Further, the control substance can be an antibody having an equivalent binding specificity as the polyvalent substance but coming from a different species than the polyvalent analyte. Using a species difference advantageously allows the selection of a noninfectious control substance in cases where the polyvalent analyte itself is infective or dangerous to persons manufacturing the device.

In another preferred embodiment, the control substance comprises an anhydrous substance that produces a color when contacted with fluid from the sample. An example of a suitable control substance according to this aspect of the present invention is anhydrous copper sulphate.

In one preferred embodiment of the present invention, the control zone is downstream from the second zone in a direction of sample flow from the first zone to the second zone. Thus, to reach the control zone, the first substance-label must pass through at least a portion of the second zone. Incorporation of a control substance into the device downstream from the second zone advantageously allows an objective means of determining that the test for detection or quantification of a polyvalent analyte has been completed. Further, a control substance can be used as an indication that the first substance-label complexes retained activity to be recognized by the polyvalent analyte.

The control substance can also be other than downstream from the second zone in order to demonstrate the retained activity of the first substrate label, without indicating when the test is completed. Additional control substances can be incorporated to indicate, for example, exposure to the air or humidity where appropriate by incorporating a control substance that changes color when exposes to air or moisture.

Where a control zone is present, a collection zone as described above, can be placed downstream from the control zone, up stream from the control zone or split into both upstream and downstream segments.

In a preferred embodiment of the present invention, the matrices are backed by, sandwiched between or incased in a housing. The housing preferably comprises a moisture-proof material such as any of a variety of plastics known to those with skill in the art and supply handling strength and a means of handling without directly touching the matrices.

The housing can be opaque and can contain words or symbols, thereupon, such as to indicate the first zone or sample application area, the second zone or detection area and control zone or to give instructions to the user of the device. If the housing is opaque and the label is detected by visual means or means requiring the transmission of visible spectrum radiation, it is contemplated by the present invention that non-opaque areas of the housing would be incorporated over one or more areas of the second zone, such as the detection zone, or control zone. The housing can further contain apertures for application of the sample or application of additional substances needed for detection of the label.

In a preferred embodiment, the device is packaged in a moisture proof, opaque package, such as sealed aluminum foil, and stored in a temperature ranging from about 2° C. to about 30° C. A desiccant can also be provided as is known to those with skill in the art.

Figure 2:
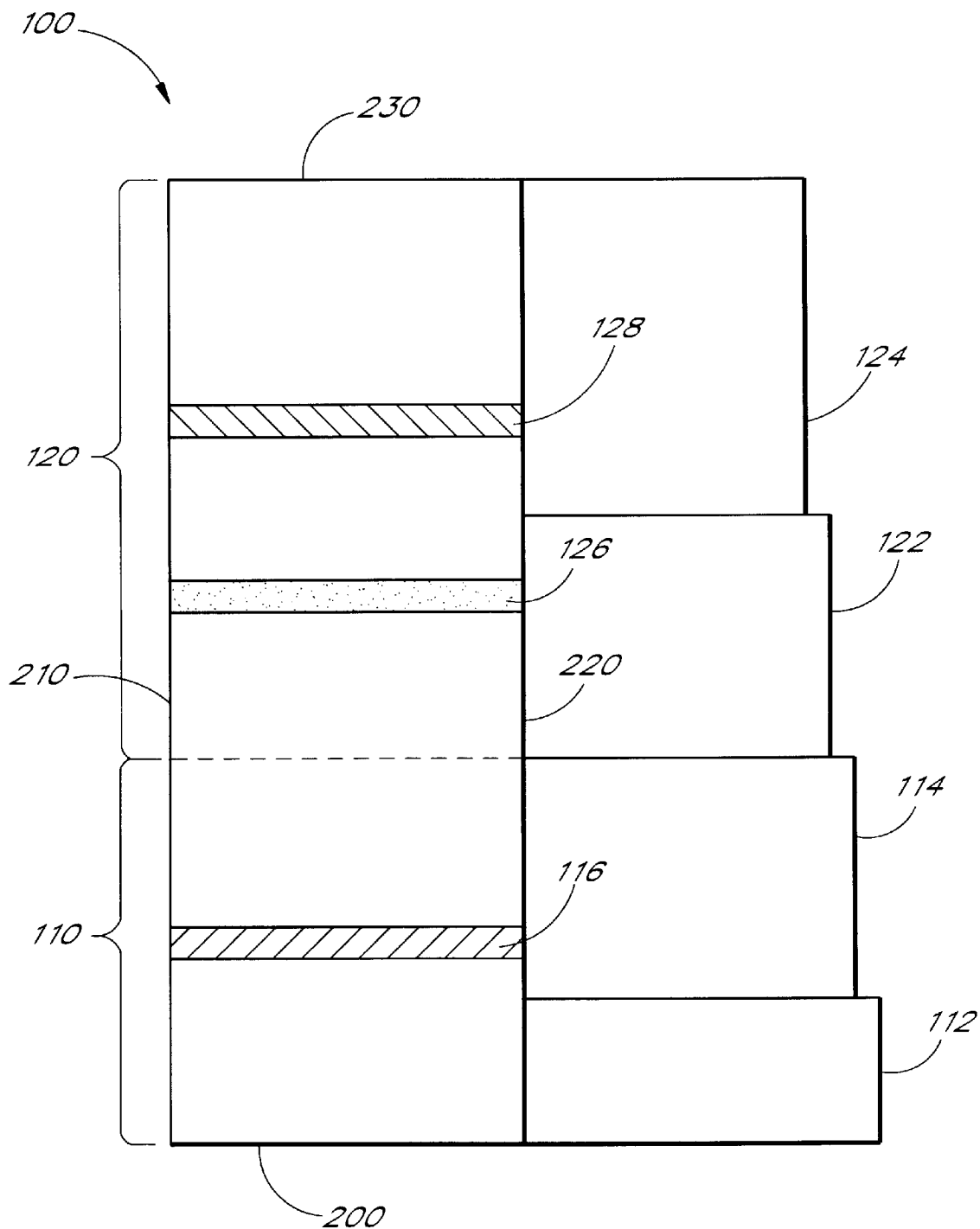
FIG. 2 is a schematic representation of an embodiment of the present invention.

Referring now to FIG. 2, a device 100 for the detection or quantification of polyvalent substance according to one aspect of the present invention is shown having a sample application end 200, a left side 210 a right side 220 and a sample collection end 230. The device is divided into a first zone 110 and a second zone 120, wherein the first zone is spatially separate from the second zone and in fluid communication with the second zone. The relative proportions illustrated in FIG. 2 were chosen for clarity rather than necessarily drawn to scale.

The first zone 110 comprises a sample application zone 112 and a separation zone 114. The separation zone 114 comprises first substance-label 116 thereupon or therewithin, as indicated by the 45° crosshatching extending from left side 210 to right side 220.

The second zone is divided into two zones, a detection zone 122 and a collection zone 124. The detection zone 112 comprises second substance 126 immobilized thereupon or therewithin, as indicated by the speckled pattern extending from left side 210 to right side 220.

The collection zone 124 comprises control substance 128 thereupon or therewithin as indicated by the 135° cross-hatching extending from left side 210 to right side 220. In one preferred embodiment, not illustrated, the control substance is part of a control zone spatially separated from the second zone and downstream from the second substance.

Figure 3:
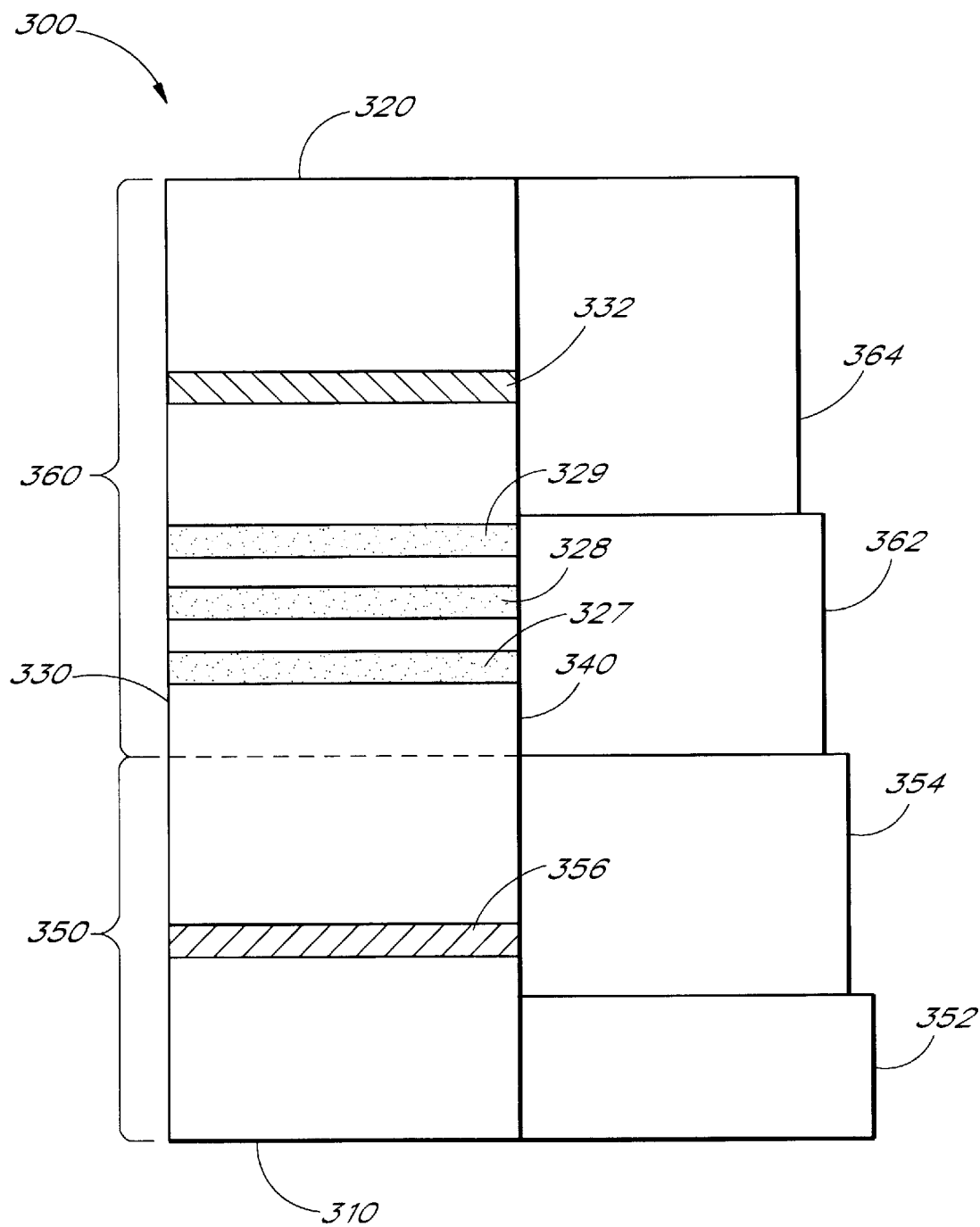
FIG. 3 is a schematic representation of an embodiment of the present invention.

Referring now to FIG. 3, a device 300 for the detection or quantification of multiple polyvalent substances according to one aspect of the present invention is shown having a sample application end 310, a left side 330, a right side 340 and a sample collection end 320. The device is divided into a first zone 350 and a second zone 360, wherein the first zone is spatially separate from the second zone and in fluid communication with the second zone. The relative proportions illustrated in FIG. 3 were chosen for clarity rather than necessarily drawn to scale.

The first zone 350 comprises a sample application zone 352 and a separation zone 354. The separation zone 354 comprises at least one first substance-label 356 thereupon or therewithin, as indicated by the 45° crosshatching extending from left side 330 to right side 340. When used to detect multiple polyvalent analytes, the at least one first substance can comprise multiple first substance-labels, such as one first substance-label for each polyvalent analyte to be detected or can comprise a single first substance-label depending on the multiple polyvalent analytes, as will be understood by those with skill in the art with reference to the disclosure herein.

The second zone is divided into two zones, a detection zone 362 and a collection zone 364. The detection zone 362 comprises at least one second substance 328 immobilized thereupon or therewithin, as indicated by the speckled pattern extending from left side 330 to right side 340. As shown, the detection zone 362 comprises multiple second substances 327, 328 and 329 immobilized thereupon. As is understood by those with skill in the art with reference to the disclosure herein, the device can comprise one second substance for each polyvalent analyte to be detected or less second substances for each polyvalent analyte to be detected.

According to a preferred embodiment of the present invention, when multiple second substances are utilized to detect multiple polyvalent analytes, the multiple second substances are separated by at least about 3 mm of second matrix and more preferably by about 5 mm of second matrix. In another preferred embodiment of the present invention, the at least one second substances is present over an at least a 1 mm wide (measuring in the direction of positive flow) horizontal strip across the device and more preferably is present over an at least a 2 mm wide strip across the device.

The collection zone 364 comprises at least one control substance 332 thereupon or therewithin as indicated by the 135° cross-hatching extending from left side 330 to right side 340. In one preferred embodiment, not illustrated, the control substance is part of a control zone spatially separated from the second zone and downstream from all of the at least one second substance.

According to a preferred embodiment of the present invention, when multiple second substances are utilized to detect multiple polyvalent analytes, the multiple second substances are separated by at least about 3 mm of second matrix and more preferably by at least about 5 mm of second matrix. This separation is particularly useful when the label or labels are to be detected visually as this spacing is conducive to determining the spatial separation of second substances.

In another preferred embodiment of the present invention, the at least one second substance is present in at least a 1 mm wide (in the direction of positive flow) horizontal strip across the device and more preferably is present in at least a 2 mm strip across the device. This strip size is particularly useful when the label or labels are to be detected visually as this size is conducive to distinguishing the presence of a colored label against a background.

The overall size of a device made according to the disclosure herein will vary with the type of use, such as whether one or multiple polyvalent analytes are to be detected. In a preferred embodiment, the overall size would be large enough to handle and use manually, while small enough to manufacture effectively. For example, the device in strip configuration as shown in FIGS. 2 and 3, without any housing can be at least about 4 mm wide and more preferably at least about 6 mm wide. Similarly, in a preferred embodiment, the device in strip configuration as shown in FIGS. 2 and 3, without any housing can be at least about 20 mm long and more preferably at least about 50 mm long. In a particularly preferred embodiment, the device is at least about 60 mm to 80 mm long.

In one preferred embodiment of the present invention, the method of detecting or quantifying polyvalent analyte present in a sample does not require the use of instrumentation after applying the sample to the device and does not require the addition of reagents to the test device after application of the sample. It is therefore, a "one-step" method, as the term is understood by those with skill in the art. The use of a standardized color chart does not qualify as the use of "instrumentation", as is understood by those with skill in the art.

In another preferred embodiment, the method of detecting or quantifying polyvalent analyte present in a sample does require the use of instrumentation after applying the sample to the device or does require the addition of fluids to the test device after application of the sample. It is therefore, a "two-step" or "multi-step" method, as the term is understood by those with skill in the art. The additional steps can include the application of non-sample fluid for a sample containing insufficient fluid and the addition of enzyme substrates or developing solutions to the location of the second substance as required to detect or quantify the label.

EXAMPLE 1

Manufacture of Device for the Detection of Antibody to HIV-1 Glycoprotein 41

In accordance with one aspect of the present invention, a device for the detection and quantification of immunoglobulin to HIV-1 envelope glycoprotein 41 was manufactured as follows. Initially, first substance-label was prepared using modified synthetic peptides and gold particles, and was impregnated onto a suitable first matrix. Next, second substance was prepared using modified synthetic peptides and immobilized onto a suitable second matrix. Finally, the test device was assembled from the first matrix impregnated with first substance-label, the second matrix containing immobilized second substance and other components. Each of these steps are discussed in greater detail below. All steps in the construction of the device were performed using clean hands techniques so as not to contaminate the device with proteins present on the skin.

(A) Preparation and Impregnation of First Substance-Label

Colloidal gold used in one aspect of the present invention, were gold particles coated with modified synthetic peptides. The gold particles had a characteristic reddish color and a diameter of between about 5 (five) and 50 (fifty) nanometers. The reddish color of the gold particles were utilized to visually detect and quantify analyte immunoglobulin. Therefore, according to one aspect of the present invention, analyte antibody were detected and quantified by a visual signal without either using additional instrumentation after applying the sample or without adding substances to the test device after applying the sample.

The preparation of first substance-label involved three procedures. First, gold particles of the proper size were prepared. Next, synthetically produced HIV-1 transmembrane or "envelope" glycoprotein 41 ("$gp_{41}$") was covalently linked to Bovine Serum Albumin ("BSA") or Bovine Serum Albumin-Lactosyl ("BSA-L") forming $gp_{41}$BSA or $gp_{41}$BSA-L, respectively. Finally, the $gp_{41}$BSA or $gp_{41}$BSA-L were conjugated with the gold particles, thereby, forming first substance. The details of these procedures are described below.

(i) Preparation of the Gold Particles

Gold particles of the proper size were produced by chemical reduction of tetrachloroauic acid with sodium citrate in a manner known to those with skill in the art. In summary, 100 ml glass distilled, 0.2µfiltered water was heated to approximately 85 to 90° C. while constantly stirring. 0.1 ml of 10% $HAuCl_4$ was added and the resultant solution boiled for about 2 minutes. Next, 0.15 ml of freshly prepared 12% sodium citrate (trisodium citrate dihydrate) was added and the solution kept boiling for about 5 minutes. The solution, which was now intensely reddish colored, was allowed to cool and stored at between 4 and 8° C. until needed.

In the alternate, gold particles were also purchased commercially from a variety of known sources, including British Biocell International of Cardiff, United Kingdom, Sigma of St. Louis, Mo. or Amersham of Arlington Heights, Ill.

(iia) Covalent Linkage of HIV-1 Envelope Glycoprotein 41 to Bovine Serum Albumin to Produce $GP_{41}$BSA Using Glutaraldehyde Next, HIV-1 envelope glycoprotein 41 ("$gp_{41}$") was linked to Bovine Serum Albumin ("BSA") in preparation for conjugation with the gold particles as follows. Synthetically produced HIV-1 peptide derived from the highly conserved N-terminal region of the transmembrane glycoprotein 41 containing twenty (20) amino acid residues 594–613 (used interchangeably with "$gp_{41}$") was obtained from Ferring Diagnostics AB, Malmo, Sweden. BSA was obtained from Sigma of St. Louis, Mo. but can be obtained from other sources known to those with skill in the art, including United States Biochemical Corporation, Cleveland, Ohio, Miles Laboratories, Elkhart, Ind. and Irvine Scientific, Santa Ana, Calif. Electron-microscopy grade Glutaraldehyde (GA) 25% was also obtained from Sigma of St. Louis, Mo. but can be obtained from other sources known to those with skill in the art, such as E. Merck, Darmstadt, Germany and ICN Biomedicals, Inc, Costa Mesa, Calif.

6.0 mg of $gp_{41}$, 13.0 mg of BSA in 2.0 ml 0.01 M PBS (pH 7.2±0.2) and 50 µl 1% GA were added to a 12×75 mm glass tube. The air was displaced with nitrogen gas and the tube was sealed with Parafilm™. The resultant solution was continuously stirred on a magnetic stir plate at room temperature for between 4 and 8 hours until moderate turbidity developed.

Fresh reducing solution of sodium cyanoborohydride ($NaCNBH_3$) was prepared containing 20 mg $NaCNBH_3$/ml distilled water. 50 µl of this reducing solution was added to the stirred mixture and stirring continued for 15–30 minutes at room temperature while the mixture was shielded from light. The resultant mixture containing conjugated $gp_{41}$BSA and unconjugated peptide was concentrated and partially purified by centrifugal ultrafiltration method at 1500×g for 15 minutes at 8° C., using Centriprep-30 concentrator from Amicon, Inc., Beverly, Mass.

Finally, the concentrated solution of about 1.5 ml of conjugated $gp_{41}$BSA was purified by applying it to a 1×25 cm Sephadex G-25 column equilibrated with 10 mM sodium phosphate, pH 7.2, containing 145 mM sodium chloride and 0.05% sodium azide (PBS). 1.0 ml fractions were collected at room temperature and the first peak containing $gp_{41}$BSA conjugate was evaluated to determine immunoreactivity with the specific human anti-$gp_{41}$ antibody. Fractions comprising the center 75 to 80% of the immunoreactive peak, were then pooled and stored at 4 to 8° C.

(iib) Covalent Linkage of HIV-1 Envelope Glycoprotein 41 to Bovine Serum Albumin-Lactosyl to Produce $GP_{41}$BSA-L In an alternate method to that disclosed in section (A)(iia), HIV-1 envelope glycoprotein 41 ("$gp_{41}$") was covalently linked to Bovine Serum Albumin-Lactosyl ("BSA-L") in preparation for conjugation with the gold particles as follows. $Gp_{41}$ was obtained from the same source identified above. BSA-L was obtained from Sigma, St. Louis, Mo., but can be obtained from other sources known to those with skill in the art.

15 mg of BSA-L was activated in a 12×75 mm glass tube by first dissolving it in 750 µl of distilled water. 50 µl of 3 molar sodium acetate was used to adjust the pH to 4.5. 100 µl of 0.1 molar periodate solution was added. The resultant solution was well mixed and allowed to incubate at room temperature for about 5 minutes.

Next, 150 µl of 0.1 molar periodate was added. The glass tube was sealed and allowed to incubate at room temperature for about 35 minutes, completing the activation step.

The activated BSA-L was purified by applying the mixture to a 1×25 cm Sephadex G-25 gel permeation column equilibrated with 0.5 mM sodium acetate and having a pH of 4.5. Fractions were collected in 1.0 ml increments. Protein containing fractions were identified by Coomassie™ Brilliant Blue G-250 dye reagent supplied by BioRad in form of a single solution as BioRad Protein Assay Dye Reagent, BioRad, Richmond, Calif. Center fractions comprising 70 to 80% of the protein peak were pooled to yield purified, activated BSA-L.

Conjugation of activated BSA-L with $gp_{41}$ was accomplished by dissolving $gp_{41}$ in distilled water and combining this solution with activated BSA-L at a ratio of 1.0 mg of $gp_{41}$ for each mg of activated BSA-L. 2.5 mg activated BSA-L in 0.6 ml 0.5 mM sodium acetate were mixed with 2.5 mg $gp_{41}$ dissolved in 125 µl distilled water and adjusted with 50 µl 0.5 M sodium carbonate to pH 9.5. The pH of the resultant solution was adjusted to 9.5 using 0.5 M sodium carbonate buffer. The solution was then incubated at room temperature for 2 hours, and followed by incubation at 2–8° C. for between 12 and 18 hours. The resultant Schiff base was stabilized by adding 0.32 M sodium cyanoborohydride solution to obtain a final concentration of 8–10 mM of sodium cyanoborohydride and incubated at room temperature for 30 minutes.

Finally, the conjugated $gp_{41}$BSA-L was purified by dialysis against 5 mM sodium borate buffer having a pH of 9.0 using a dialysis membrane tubing with a molecular weight cut-off of 12,000 to 14,000, obtained from Spectrum Medical Industries, Inc., Los Angeles, Calif. The buffer was changed 4 to 6 times during 24–48 hours of dialysis using a magnetic stir plate at 4 to 8° C. The purified conjugated $gp_{41}$BSA-L was stored at 4–8° C.

(iii) Conjugation of Envelope Glycoprotein 41/Bovine Serum Albumin or Envelope Glycoprotein 41/Bovine Serum Albumin-Lactosyl with the Gold Particles to Produce First Substance-Label Both $gp_{41}$BSA and $gp_{41}$BSA-L, as prepared by the methods disclosed in sections (A)(iia) or (A)(iib) above, respectively, are suitable for conjugation with the gold particles and were used to produce first substance-label. Initially, the minimal amount of $gp_{41}$BSA or $gp_{41}$BSA-L needed to fully stabilize the suspension of gold particles, prepared in step (A)(i) above, was determined as follows.

1 milliliter aliquots of gold solution were dispensed into 12×75 mm glass test tubes. The pH was adjusted to between 7.2 and 7.5 using 40 µl of 0.25 M sodium borate having a pH of 7.25. 10 to 100 µl containing known quantities of $gp_{41}$BSA or $gp_{41}$BSA-L were then added to the test tubes. The resultant solutions were mixed and incubated at room temperature for 5 minutes. Finally, 100 µl of 10% sodium chloride solution were added to each test tube.

After an additional 5 minutes the change in color of colloidal gold suspension was recorded. Retention of the reddish color indicated stabilization of the gold particles by the corresponding quantity of the peptide-BSA conjugate. Loss of the reddish color and appearance of a purple or blue color indicated aggregation of the gold particles by the high salt concentration of sodium chloride and, therefore, insufficient quantity of protecting peptide-BSA conjugate. The minimum quantity of peptide-BSA conjugate which retained the reddish color of the gold particles was considered as the stabilizing concentration and was used for future gold-peptide BSA conjugate preparation. Using this method, it was found that 25 µg of $gp_{41}$BSA, or alternately 25 µg of $gp_{41}$BSA-L, gave optimal stabilization of 30 nm gold particles to be linked with the above peptide-BSA molecules.

After the above determination was made, 70 ml of the suspension of 30 nm gold particles was dispensed into a clean glass Erlenmeyer flask. The pH of the suspension was adjusted to between 7.2 and 7.5 using 0.25 M sodium borate having a pH of 7.25.

Next, 1750 µg of $gp_{41}$BSA or $gp_{41}$BSA-L was dissolved in 1.0 ml of 10 mM of sodium borate buffer and was added to the suspension of gold particles. The resultant diluted suspension was mixed gently and incubated at room temperature for 5 minutes.

After incubation, 1.4 ml of 10% sterile Bovine Serum Albumin, obtained by dissolving 10 gm of BSA from Sigma, St. Louis, Mo. in 100 ml of distilled water and filtering the solution with a 0.2µ filter, was added to the diluted suspension and mixed well. The diluted suspension was incubated at room temperature for 30 minutes.

The gold particle bound/$gp_{41}$BSA or gold particle bound/$gp_{41}$BSA-L was separated from the unbound $gp_{41}$ BSA or unbound $gp_{41}$BSA-L, respectively, by centrifuging the diluted suspension at 28,000×g for 45 minutes at 8° C. The supernatant was carefully aspirated. The pellet was resuspended using 0.1% polyethylene glycol (PEG) 20 K in 0.01 M borate having a pH of 9.0. in a volume equal to that aspirated. The centrifugation, aspiration and resuspension steps were repeated at least two time more for a total of 3 or 4 times. The final resuspended pellet contained the gold particle bound/$gp_{41}$BSA or gold particle bound/$gp_{41}$BSA-L, that is, the first substance-label. It was stored at 4° C. in 0.1% PEG 20 K in 0.01 M borate having a pH of 9.0 at 25 to 35 times the starting concentration of gold particle suspension, that is, 2.8 to 2.0 ml, respectively for the above conjugation starting with 70 ml of gold.

(iv) Impregnation of First Substance-Label Onto the First Matrix

As used hereinafter, "$gp_{41}$Au" refers to either gold particle bound/$gp_{41}$BSA or gold particle bound/$gp_{41}$BSA-L, prepared and purified by the methods disclosed above. The first matrix used was derived from glass fiber sheets, 28.5× 21.5 cm and 0.4 mm thick available from Lydall Manning Co., Troy, N.Y., though other sources are known to those with skill in the art.

A diluent, Gold Conjugate Dilution Buffer 1, was prepared by containing 50 mM Tris, 1.0% BSA, 0.5% PEG 15–20 K, 0.3% PVP 30 K, 2.5% sucrose and 0.9% T-20. The solution had a pH of 7.3 and was filtered using a 0.45µ pore size filter. 40 ml of a diluted suspension of $gp_{41}$Au was prepared by mixing 3.33 ml of $gp_{41}$Au suspension with 36.67 ml of diluent yielding a titre of 1:12.

The resultant diluted suspension was gently mixed and incubated at room temperature for 5–10 minutes. One glass fiber sheet was placed in a suitable plastic tray of dimensions slightly longer than the first matrix sheet. 40 ml of diluted suspension was then uniformly distributed over the entire area of the first matrix by rapidly dispensing the suspension on the matrix followed by immediately tilting the plastic tray carrying the matrix in the direction of the unwetted portion of the matrix. Uniform distribution of the gold suspension was detected visually through uniform reddish staining of the entire matrix.

The diluted suspension-covered first matrix was allowed to stand for 10–15 minutes at room temperature. Then, the diluted suspension-covered first matrix was transferred onto a wire mesh tray where it was dried under vacuum at ambient temperature for 1.5 to 2.0 hours, completing production of a first substance-label-impregnated first matrix. The finished impregnated first matrix was stored in a desiccated container pending incorporation into the finished test strip.

(B) Preparation and Immobilization of Second Substance

The next steps involved the preparation of the second substance and immobilization of second substance onto the second matrix. The second substance comprised $gp_{41}$BSA or $gp_{41}$BSA-L prepared according to the methods described above. This second substance was diluted in phosphate buffered saline having a pH of 7.4 to a concentration of between 1–4 mg/ml.

The second matrix comprised nitrocellulose membrane having a pore size of between about 6 and 15µ. Suitable nitrocellulose membrane is available from Schleicher & Schuell, Keene, N.H. or Gelman Sciences, Ann Arbor, Mich., among other sources known to those with skill in the art.

The second substance was immobilized onto the second matrix by microprocessor-controlled airbrush spraying. A microprocessor-controlled airbrush was used because it gave repeatable results. A narrow, approximately 1–2 mm wide, strip of second substance was centrally deposited approximately 10–13 mm from the edge of a 25 mm wide by 50 meters long nitrocellulose membrane roll. The immobilized second matrix was dried at room temperature for 20–60 minutes and then dried under vacuum for 1.5 to 2.0 hours.

(C) Assembly of Device

A working device was assembled as follows. Liquid absorber pad strips 18×295 mm, and sample absorber pad strips 20×295 mm, were cut from cellulose absorber sheets supplied by Gelman Sciences, Ann Arbor, Mich. Other sources of cellulose absorber sheets are known to those with skill in the art, including Whatman Specialty Products, Fairfield, N.J. and Schleicher & Schuell, Inc., Keene, N.H.

First matrix containing first substance-label were cut into 8×295 mm strips. Second matrix containing immobilized second substance were cut into 30 cm long strips. Vinyl plastic backing with adhesive 59×290 mm long was obtained from G&L Precision Die Cutting, Inc., Campbell, Calif.

A second matrix strip was affixed to the vinyl plastic backing 19 mm from the bottom edge of the backing. A liquid absorber pad strip was laid on top of the backing overlapping 1 to 2 mm of the top edge of the second matrix strip. Next, a first matrix strip was laid on the backing overlapping about 1 mm of the bottom edge of the second matrix strip. Finally, a sample absorber pad strip was laid at the bottom of the backing such that the sample absorber pad touched the first matrix strip.

The backing was turned over and placed on a flat surface. Uniform pressure was applied to the backing to affix the strips. Next, the backing with the affixed strips were cut into 8 mm sections perpendicular to the long axes of the strips. Finally, the sections were placed in a suitable plastic housing completing the assembly.

Figure 4:
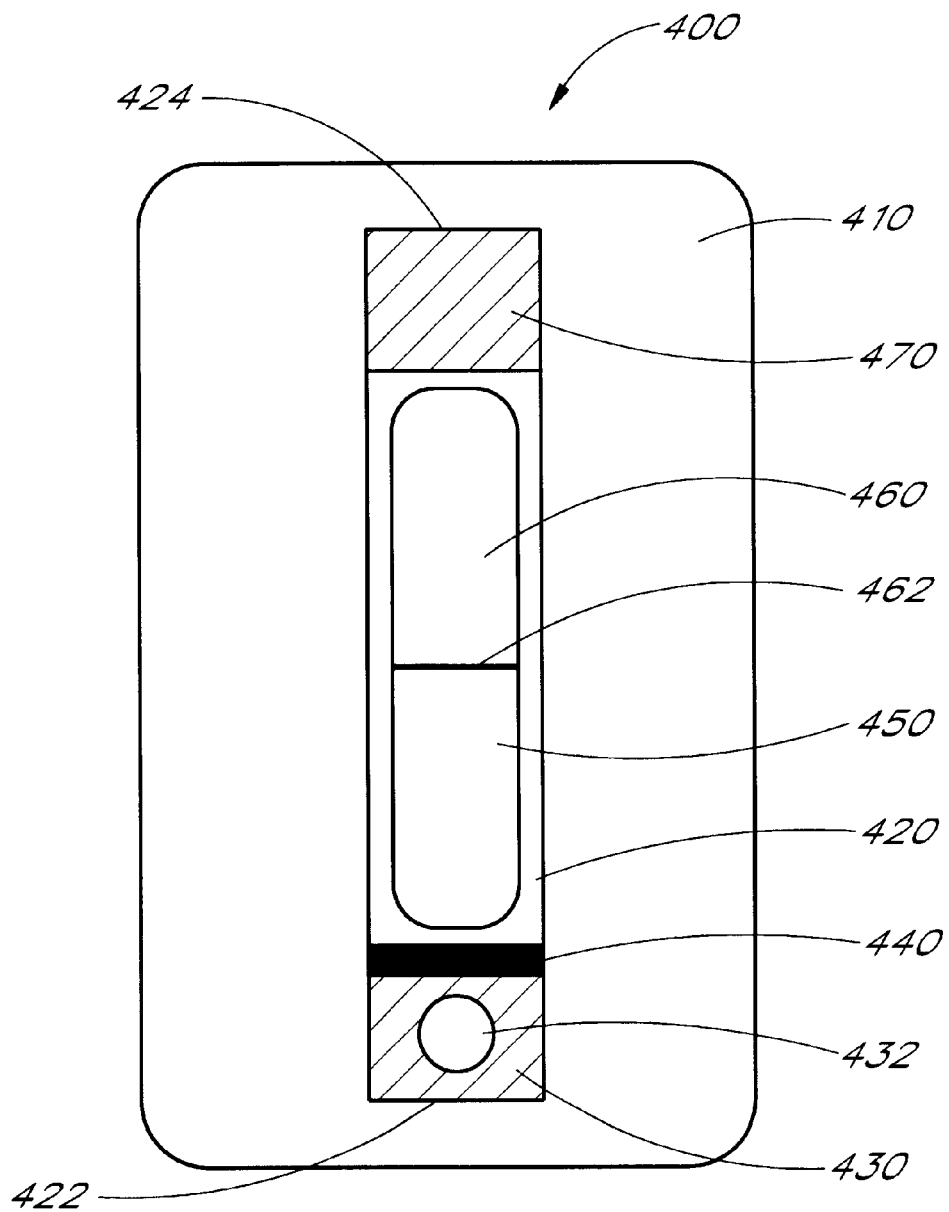
FIG. 4 is a schematic representation of an embodiment of the present invention.

Referring now to FIG. 4, there is shown an assembled test device 400 according to one aspect of the present invention. The test device 400 has a plastic housing 410 containing a test strip 420. The test strip 420 comprises a sample application end 422 and a sample collection end 424. At the sample application end 422 of the test strip 420 is a sample absorber pad 430 having a sample application port 432. Adjacent the sample absorber pad 430 is a first substance 440. A test window 450 in housing 410 reveals the second matrix 460 and immobilized second substance 462, thereupon. At the sample collection end 424 is a liquid absorber pad 470.

EXAMPLE 2

Method of Use of Device for the Detection of Antibody to HIV-1 Glycoprotein 41

In accordance with another aspect of the present invention, there is provided a method of using a test device for the detection or quantification of antibody to AIDS virus as follows. A test device was made according to Example 1 above. Referring now to FIG. 4, four drops, equal to about 200 μl, of sample fluid obtained from either human serum or human plasma and containing analyte antibody to HIV-1 envelope glycoprotein 41 virus was applied to the sample port 432 over the sample absorber pad 430 using a plastic disposable pipette.

Sample moved through the sample absorber pad 430 encountering first substance-label upon entering the first matrix 440. At least some of the analyte antibody in the sample was bound to first substance-label by one of the at least two epitope binding sites present on the analyte antibody, thereby, forming analyte antibody/first substance-label complexes (antibody to HIV-1 envelope glycoprotein 41 virus/$gp_{41}$/Au complexes). At least some of these complexes moved though the first matrix into the second matrix 460 where they encountered immobilized second substance 462. At least some of the complexes that encountered immobilized second substance was bound to the immobilized second substance by one of the at least two binding sites present on the analyte antibody, thereby, forming immobilized second substance/analyte antibody/first substance-label complexes (immobilized $gp_{41}$/antibody to HIV-1 envelope glycoprotein 41 virus/$gp_{41}$/Au complexes). Unbound sample components and unbound analyte antibody/first substance-label complexes continued to flow past the immobilized second substance towards the liquid absorber pad 470 at the sample collection end 424 of the test device.

The gold particles immobilized to the second matrix through the second substance turned the location of the second substance a visually detectable reddish color that was detectably more color saturated than the rest of the second matrix visible through the test window 450. A greater intensity of reddish color at the location of the second substance indicated the presence of a greater amount of antibody to HIV-1 $gp_{41}$ in the sample. The test was completed in less than about 3–5 minutes after application of the sample fluid to the sample application port 422.

The specificity of the device according to one aspect of the present invention was tested using a sample of serum or plasma that did not contain antibody to HIV-1 $gp_{41}$. The sample was applied to a test device 400 at the sample application port 432. After allowing the sample fluid 5 minutes to traverse the device from sample application pad 430 to liquid absorber pad 470, no characteristic reddish color was present at the location of the second substance, beyond that present essentially throughout the second matrix.

The sensitivity of the device for the detection of antibody to HIV-1 $gp_{41}$ according to one aspect of the present invention was tested by comparing the results of 242 samples evaluated using both the present device and a commercially available test. Comparing the results against an indirect, Elisa test employing alkaline phosphatase anti-human IgG conjugate, as is well known to those with skill in the art, sixty five (65) samples were identified by both assays as negative and one hundred seventy seven (177) specimens were identified by both assays as positive for HIV-1 related antibodies. Comparing the results obtained with the present device for a Mixed-Titer Performance Panel, PRB 202 from Boston Biomedica, Inc., Bridgewater, Mass., twenty-five (25) samples yielded a specificity of 100%, and a sensitivity of 96% based on two FDA licensed Western Blot procedures or 100% when correlated with a third FDA licensed Western Blot. Further, the device for the detection of antibody to HIV-1 $gp_{41}$ according to one aspect of the present invention correctly identified the seroconversion sample from a Seroconversion Panel J, PRB 910 supplied by Boston Biomedica, Inc. in complete agreement with other FDA approved HIV-1 antibody Elisa procedures.

EXAMPLE 3

Device and Method of Use for the Detection of Antibody to HIV-2 Glycoprotein 36

Analyte antibody to HIV-2 glycoprotein 36 was detected using a device and method analogous to the embodiment described above in Example 1 and Example 2 above for the detection of immunoglobulin to HIV-1 glycoprotein 41. A summary of the construction of the device is as follows:

(A) Preparation and Impregnation of First Substance-Label (i) Preparation of the Gold Particles Gold particles of the proper size were produced as described under Example 1(A)(i), above.

(ii) Covalent Linkage of HIV-2 Envelope Glycoprotein 36 to Bovine Serum Albumin to Produce $GP_{36}BSA$ Using Glutaraldehyde The first substance used comprised synthetically produced HIV-2 peptide encoded by the highly conserved region of the virus envelope gene. The peptide contained amino acids 585–603, had a molecular weight of 2412 and was obtained from Ferring Diagnostics AB, Malnio, Sweden. It is referred to in this Example as "$gp_{36}$".

Using an analogous method to the method described under Example 1(A)(iia), 3 mg of $gp_{36}$ were added to 6.0 mg BSA dissolved in 1.0 ml PBS, pH 7.2. 25 $\mu$l 1% glutaraldehyde was then added to the solution and the solution was stirred at room temperature for 3.5 hours. Next, 25 $\mu$l of freshly prepared sodium cyanoborohydride solution, having a concentration of 20 mg/ml distilled water, were added to the solution and stirring continued for 15 minutes at room temperature. Finally, the resultant $gp_{36}$ BSA conjugate was purified on a 18×1.6 cm Sephadex G-25 column equilibrated with PBS. Fractions were collected, evaluated for presence of immunoreactive conjugate, pooled and stored as described above.

(iii) Conjugation of Envelope Glycoprotein 36/Bovine Serum Albumin with the Gold Particles to Produce First Substance-Label Conjugation of $gp_{36}$ Bovine Serum Albumin ($gp_{36}$BSA) to the gold particles was achieved in analogy to the procedure outlined under Example 1(A)(iii), above. Briefly, after determination of the stabilizing concentration of $gp_{36}$BSA as being equal to 15 $\mu$g per milliliter of the 30 nm gold particles, 3750 $\mu$g $gp_{36}$ in 5 ml 10 mmolar sodium borate, pH 7.3 were added to 250 ml of gold particles also at pH 7.3. The resultant solution was mixed and incubated for ten (10) minutes at room temperature.

Next, five (5) ml of 0.2$\mu$ filtered 10% BSA/ml distilled water was added and the solution incubated at ambient temperature for one (1) hour. Separation of gold particle bound from unbound $gp_{36}$BSA was accomplished by a centrifugation/aspiration/resuspension cycle repeated three times. Finally, the purified $gp_{36}$BSAAu conjugate was reconstituted in 10 ml 0.1% PEG 20 K in 0.01 M borate pH 9.0 to a concentration of 2.5 mg gold particles per milliliter suspension. The solution was stored at 4° C.

(iv) Impregnation of First Substance-Label Onto the First Matrix

To prepare $gp_{36}$BSAAu conjugate for impregnation of glass fiber sheets, in a method analogous to that of Example 1(A)(iv), the concentrated suspension of $gp_{36}$BSAAu was diluted 1:12 fold (3.33 ml conjugate were added to 36.67 ml diluent) with the 0.45$\mu$ filtered Gold Conjugate Dilution Buffer 1 containing 1% BSA, 0.5% PEG 15–20 K, 0.3% PVP 30 K, 2.5% Sucrose and 0.9% T-20 in 50 mmolar Tris buffer pH 7.3. Application of diluted conjugate to glass fiber sheet, drying and storage of impregnated first matrix was same as outlined above.

(B) Preparation and Immobilization of Second Substance

The preparation and immobilization of the second substance, $gp_{36}$BSA, was performed in a method analogous to that of Example 1(B), above.

(C) Assembly of Device

A working device for the detection and quantification of immunoglobulin to HIV-2 envelope glycoprotein 36 was assembled manufactured in a method analogous to that of Example 1(C), above.

EXAMPLE 4

Manufacture of Device for the Co-Detection of Antibody to HIV-1 Glycoprotein 41 and HIV-2 Glycoprotein 36

According to one aspect of the present invention, a test device for co-detection of HIV-1 glycoprotein 41 and HIV-2 glycoprotein 36 was constructed using processes analogous to those given in Examples 1 and 3, above. The device comprised first matrix impregnated with first substances $gp_{41}$BSAAu and $gp_{36}$BSAAu, and second matrix containing immobilized second substances $gp_{41}$BSA and $gp_{36}$BSA.

40 ml of first substance was prepared by addition of 3.33 ml of $gp_{41}$BSAAu and 3.33 ml of $gp_{36}$BSAAu stock suspension to 33.34 ml Gold Conjugate Dilution Buffer 1. The first substance was mixed and impregnated on glass fiber sheets. The sheets were dried by vacuum and stored under desiccation until used.

Second substances $gp_{41}$BSA and $gp_{36}$BSA were diluted in PBS, pH 7.4, to a concentration of 2.2 and 1.6 mg per milliliter, respectively. The second substances were sprayed onto a 12$\mu$ pore size nitrocellulose membrane using airbrush #1 to apply $gp_{41}$BSA as a narrow 1–2 mm line 10 mm from bottom edge of second matrix, and airbrush #2 to apply $gp_{36}$BSA as a narrow line 15 mm from bottom edge of second matrix. The second matrix was dried at room temperature for approximately 30 minutes, and then under vacuum for between approximately 1.5 to 2.0 hours and stored under desiccation until used.

EXAMPLE 5

Method of Manufacturing Control Substance for Use with the Test Device of Examples 1, 3 and 4

According to one aspect of the present invention, a control substance comprising a monoclonal antibody to BSA was manufactured for use with the test devices described in the above Example 1, 3 and 4. The control substance captured all gold-labelled, synthetic peptide-BSA conjugates (first substance), that had not reacted with second substance, by specific immunological reaction with epitopes present on the BSA moiety. The reddish color of the captured conjugates served as a visually identifiable marker indicating the viability of the test device and the completion of the test. The control substance was manufactured as follows.

Partially purified, Ammonium Sulfate (A.S.) precipitated and dialyzed, monoclonal Anti BSA antibody was obtained from Beckman Instruments, Inc. Carlsbad, Calif., USA. The monoclonal antibody was dissolved in 10 mM of sodium phosphate buffer having a pH 7.4, 145 mM sodium chloride (PBS) to obtain a concentration of 1–2 mg/ml. The dissolved monoclonal antibody was immobilized onto the second matrix about 19 mm from the bottom edge of the matrix for the devices of Examples 1, 3 and 4, employing the same airbrush microprocessor unit as for the spraying of $gp_{41}$BSA in Example 1(B), above.

Competitive inhibition by Bovine Serum Albumin contamination will inhibit, partially or completely, the limited capacity of the immobilized Anti BSA antibody to bind the $gp_{41}$BSAAu or $gp_{36}$BSAAu. Therefore, in order to permit immunological recognition of the BSA moiety linked to the $gp_{41}$BSAAu or $gp_{36}$BSAAu conjugate by the immobilized Anti BSA antibody, the Gold Conjugate Dilution Buffer used in the preparation of the immobilization solution had to be substantially completely free of any Bovine Serum Albumin contamination.

The Gold Conjugate Dilution Buffer used previously for dilution of $gp_{41}$BSAAu or $gp_{36}$BSAAu in Example 1 and Example 3, above, respectively, contained 1% BSA to stabilize the gold conjugate in the impregnating solution. Therefore, this buffer was replaced by 0.2% Human Serum Albumin in otherwise unchanged Gold Conjugate Dilution Buffer.

Second substances $gp_{41}$BSA, $gp_{36}$BSA prepared as in Example 4 were applied on second matrix as line 1 and line 2, 10 mm and 15 mm, respectively, from the bottom edge of the 25 mm wide nitrocellulose membrane strip, together with partially purified monoclonal Anti BSA antibody at 1–2 mg/ml PBS, as line 3, 19 mm from the bottom edge of the membrane. A set up of three airbrushes were employed for uniform, consistent application of all three reagents. The sensitized second matrix was dried at room temperature and by vacuum as discussed previously, stored in desiccated container.

The present invention can be embodied in other specific forms without departing from its spirit or essential characteristics. The described embodiments are to be considered in all respects only as illustrative and not restrictive. The scope of the invention was, therefore, indicated by the appended claims rather than the foregoing description. All changes which come within the meaning and range of equivalency of the claims are to be embraced within their scope.

I claim:

1. A device for detecting the presence or amount of HIV-1 or HIV-2 antibody in a biological sample, comprising:
   a sample absorber pad for application of said sample;
   a first matrix, said first matrix being in fluid communication with said sample absorber pad, said first matrix being impregnated with a first glycoprotein covalently linked to bovine serum albumin, said first glycoprotein being selected from the group consisting of HIV-1 glycoprotein 41 and HIV-2 glycoprotein 36, said glycoprotein covalently linked to bovine serum albumin being conjugated with gold particles having a diameter of between about 5 nm and about 50 nm; and
   a second matrix in fluid communication with the first matrix, said second matrix having immobilized thereon at a point spatially separated from the first matrix a second glycoprotein covalently linked to bovine serum albumin, said second glycoprotein being HIV-1 glycoprotein 41 when said first glycoprotein is HIV-1 glycoprotein 41 and being HIV-2 glycoprotein 36 when said first glycoprotein is HIV-2 glycoprotein 36, said second glycoprotein being immobilized on the second matrix;
   wherein the first glycoprotein is capable of moving from the first matrix to the second matrix and to said point spatially separated from the first matrix after application of the sample to the first zone.

2. The device of claim 1, wherein said bovine serum albumin is bovine serum albumin-lactosyl.

3. The device of claim 1, wherein the second matrix comprises nitrocellulose.

4. The device of claim 1, wherein the first matrix comprises a glass fiber sheet.

5. The device of claim 1, wherein the sample application pad at least partially overlays the first matrix.

6. The device of claim 1, wherein said second matrix has a first end and a second end, wherein said first end is in fluid communication with said first matrix, said device additionally comprising a liquid absorber pad in fluid communication with the second end of said second matrix.

7. The device of claim 1, wherein the second matrix further comprises a control substance immobilized thereupon at a second point apart from the point where the second glycoprotein is immobilized and also apart from the first matrix.

8. The device of claim 7, wherein the control substance comprises antibody to bovine serum albumin.

9. The device of claim 1, wherein each of said sample application pad, first matrix and second matrix are attached to a vinyl backing.

10. The device of claim 1 adapted for detection of HIV-1 and/or HIV-2, wherein said first matrix is impregnated with both HIV-1 glycoprotein 41 and HIV-2 glycoprotein 36, and wherein said second matrix has both HIV-1 glycoprotein 41 and HIV-2 glycoprotein 36 immobilized therein at separate points spatially separated from the first matrix.

11. A method for detecting the presence or amount of analyte antibody to Human Immunodeficiency Virus (HIV) in a sample, said method comprising the steps of:
   a) providing a device according to claim 1;
   b) applying the sample to the sample application pad, said antibody in said sample comprising first and second epitope binding sites;
   c) binding the first epitope binding site on the analyte antibody to the first epitope on the first glycoprotein, thereby forming an analyte antibody/first glycoprotein complex;
   d) allowing the analyte antibody/first glycoprotein to migrate from the sample application pad to the first matrix and then to the second matrix;
   e) allowing the second epitope binding site on the analyte antibody of the analyte antibody/first glycoprotein to bind to the second epitope on the immobilized second glycoprotein in the second zone, thereby forming immobilized first glycoprotein/analyte anti body/second glycoprotein; and
   f) visually determining the presence of gold particles upon the first glycoprotein of the immobilized first glycoprotein/analyte antibody/second glycoprotein, wherein detection of the label is an indication of presence or amount of the analyte antibody to HIV.

12. The method of claim 11, wherein the sample is selected from the group consisting of serum and plasma.

13. The method of claim 11, wherein the application step, step b), comprises spotting the sample on the sample application pad.

14. The method of claim 11, further comprising the step of filtering the sample between the providing step, step a), and the applying step, step b).

* * * * *